United States Patent [19]

Wu et al.

[11] Patent Number: 5,440,022
[45] Date of Patent: Aug. 8, 1995

[54] HEPATOKINE AND METHODS FOR ITS USE

[75] Inventors: Chu-tse Wu; Qiang Tu; Fu-chu He, all of Beijing, China; James W. Larrick, Woodside, Calif.

[73] Assignee: Panorama Research, Inc., Mountain View, Calif.

[21] Appl. No.: 961,276

[22] Filed: Oct. 14, 1992

[51] Int. Cl.$^6$ .................. A61K 38/00; C07K 14/00
[52] U.S. Cl. .................................. 530/399; 435/240.2
[58] Field of Search ................. 514/12, 21; 530/399; 435/240.2

[56] References Cited

U.S. PATENT DOCUMENTS 5,004,805  4/1991  Gohda et al. ............... 530/324

Primary Examiner—Howard E. Schain
Assistant Examiner—Lynn Touzeau
Attorney, Agent, or Firm—Townsend and Townsend Khourie and Crew

[57] ABSTRACT

A novel human hepatokine, referred to hereinafter as HPX, has been isolated and purified from human fetal hepatocytes. HPX has a molecular weight of approximately 15 kD, a pI of about 6, and has been found to promote hepatocyte growth activity in vitro and in vivo.

2 Claims, 3 Drawing Sheets

HEPATOKINE AND METHODS FOR ITS USE

BACKGROUND OF THE INVENTION

1. Field of the Invention

The present invention relates generally to the isolation, production, and use of growth factors. More particularly, the present invention relates to a novel therapeutic hepatokine which may be isolated and purified from mammalian cells.

Autocrine and paracrine growth factors for liver tissue are referred to generally as hepatokines. Presently known hepatokines include hepatocyte growth factor (HGF, previously referred to as hepatopoietin A), hepatopoietin B, and the like. HGF is a 728 amino acid, 83 kD heterodimeric protein which stimulates adult hepatocytes and which has been found to be identical to tumor cytotoxic factor released by embryonic lung diploid fibroblasts. Hepatopoietin B is a glycolipid having relatively weak mitogenic activity and a low molecular weight. Other cytokines having non-specific hepatocyte growth stimulating activity include epidermal growth factor (EGF), transforming growth factor-$\alpha$ (TGF-$\alpha$), transforming growth factor-$\beta$ (TGF-$\beta$), platelet-derived growth factor (PDGF), and acidic and basic fibroblast growth factor (FGF).

The ability to promote the growth and repair of liver cells would be of value in the treatment of a number of diseases and conditions. Liver dysfunction secondary to viral infection, alcohol abuse, and exposure to hepatotoxins, is a leading cause of morbidity and mortality. In particular, liver dysfunction is problematic because of a lack of suitable therapies.

It would therefore be desirable to provide novel hepatocyte growth factors capable of promoting the growth and repair of liver cells, particularly for the treatment of diseases, such as acute and chronic hepatitis, alcoholic liver diseases, liver dysfunction due to sepsis, exposure to toxins, and the like. Such growth factors would also be useful in conjunction with liver transplantion as well as in the culture of liver cells, particularly in conjunction with hepatocyte gene therapy.

2. Description of the Background Art

Hepatocyte growth factor (HGF) is described in Michalopoulos (1992) Hepatology 15:149–155. Hepatopoietin B is described in Michalopoulos et al. (1984) Cancer Res. 44:4414–4419. Other growth factors having hepatocyte growth stimulating activity are described in Kost et al. (1991) J. Cell Physiol. 147:274–280; Mead et al. (1989) Proc. Natl. Acad. Sci. USA 86:1558–1562; and Kan et al. (1989) Proc. Natl. Acad. Sci. USA 86:7432–7436. An assay for assessing the activity of hepatokines is reported in Tu and Wu (1990) Chinese J. Appl. Physiol. 6:199–203 and (1991) Chinese J. Pathophysiol. 7:537–541.

The full disclosures of each of the above papers are incorporated herein by reference.

SUMMARY OF THE INVENTION

A novel hepatokine, referred to hereinafter in the claims as hepatopoietin X (HPX), has been isolated and purified from mammalian cells. In particular, human HPX has been isolated from a soluble lysate of human fetal liver cells and purified to substantial homogeneity, where purification was monitored using a hepatocyte mitogenesis assay. The purified HPX provides a single 15 kD band on both SDS-PAGE and capillary electrophoresis. Other physical and biochemical properties of HPX are set forth in detail in the Experimental section hereinafter.

HPX compositions are useful for in vitro and in vivo hepatocyte stimulation. In particular, HPX may be incorporated into pharmaceutical compositions useful for in vivo treatment of liver diseases and conditions. In vitro uses include growth promotion in hepatocyte cell culture, for example, in growing hepatocytes for gene therapy applications.

DESCRIPTION OF SPECIFIC EMBODIMENTS

Figure 1:
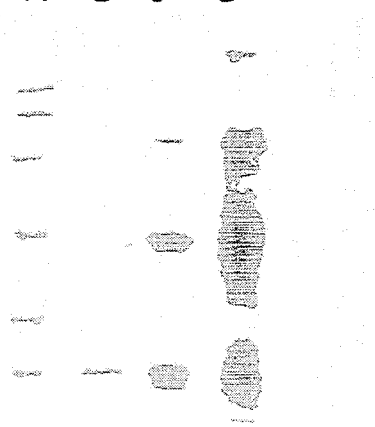
FIG. 1 is a 10%–20% SDS-PAGE of human HPX at different stages of purification, as described in the Experimental section hereinafter. Lane A includes the following size markers: phosphorylase B (97.4 kD); bovine serum albumin (66.2 kD); ovalbumin (45 kD); carbonic anhydrase (31 kD); soybean trypsin inhibitor (25 kD); and lysozyme (14.4 kD). Lane B is HK-4; lane C is HK-3; and lane D is HK-2.

According to the present invention, a novel hepatokine has been discovered which displays hepatocyte-specific growth stimulatory (mitogenic) activity. The novel hepatocyte has been designated HPX and in humans has been found to have a molecular weight of about 14 kD ($\pm$3kD), a pI of about 6, and other specific biochemical and physical characteristics as set forth in detail in the Experimental section hereinafter.

Based on this discovery, HPX can be obtained from both natural and synthetic sources. Natural HPX may be isolated and purified from a variety of mammalian cellular sources, including hepatocytes, particularly including fetal hepatocytes, from humans, mice, rats, guinea pigs, rabbits, sheep, goats, cows, and particularly from humans. Cells from these sources may be collected and disrupted to produce a lysate. As an initial purification step, the lysate may be heated, for example to about 95° C., to denature other proteins. HPX has been found to be heat stable. Cellular and other debris from the resulting lysate may be separated, for example, by centrifugation, and the resulting supernatant subjected to a series of conventional purification steps. For example, proteins larger than 15 kD may be removed by ultrafiltration, and the resulting filtrate subjected to various chromatographic separation techniques until a desired level of purity is attained. At each stage, purity may be monitored using a hepatocyte mitogenic activity assay, such as the assay set forth in section 2 of the Experimental section hereinafter. A particular protocol for the isolation and purification of human HPX to substantial homogeneity is set forth in detail in the Experimental section hereinafter. An alternative hepatocyte mitogenic assay can be based on radio-labeled thymidine incorporation using a Matrix 96 Packard scintillation counter.

HPX will be present in the compositions of the present invention in at least partially purified form, typically being at least about 10% (w/w) pure and being free from the contaminants and the substances which interfere with the desired hepatocyte mitogenic activity. Usually, the HPX will be at least 25% w/w pure, more usually being at least 50% w/w pure, and preferably being at least about 75% w/w pure, or higher. In many cases, it will be desirable to obtain substantially pure (homogeneous) compositions of the HPX of the present invention, typically being greater than 90% w/w pure, preferably being greater than 95% w/w pure, and sometimes being 99% w/w pure or higher. Compositions having such high purity can be obtained using conventional protein purification techniques in conjunction with the hepatocyte mitogenic activity assay described in the Experimental section hereinafter.

Synthetic preparation of HPX may be based on sequencing of the protein or cDNA by conventional techniques. Initially, studies have shown that human HPX has a blocked N-terminus, necessitating proteolytic treatment of the protein prior to partial sequencing. Proteolytic fragments may be obtained after enzymatic hydrolysis with trypsin or other common proteolytic enzymes. The resulting fragments may be separated, e.g. by reversed-phase HPLC, followed by sequencing on commercially available protein sequencers, such as an Applied Biosystems 477A sequencer.

Based on the sequences of such internal peptides, degenerate oligonucleotide probes may be prepared in order to screen a suitable gene library, such as a human fetal liver cDNA library. Such human fetal liver cDNA libraries are commercially available from Clonetech Labs (Palo Alto, Calif.) in both λgt10 and λgt11 (Catalog Nos. HL1064a and HL1064b).

These cDNA libraries may be screened by a variety of conventional techniques for identifying the cDNA which encodes the HPX of the present invention. Such techniques include direct hybridization, polymerase chain reaction (PCR)-amplified hybridization, the use of anti-HPX antibodies, and the like. The identification of putative HPX cDNA sequences can be confirmed by introducing the recombinant λ DNA inserts into an appropriate plasmid vector for expression in an appropriate host, with the resulting expression product mapped by restriction enzyme cleavage and Southern blotting. Internally consistent clones will then be sequenced, with an internally consistent sequence being confirmed for HPX.

The identification and sequencing of HPX cDNA may be accomplished for other species in addition to human, using the general techniques described above. For most purposes, and in particular for human therapy, use of the human HPX will be preferred.

The purified HPX compositions of the present invention may be natural, i.e. including the entire HPX protein or fragments thereof isolated from the natural source, as described above, or may be synthetic, i.e. including the entire protein, or a fragment or analog thereof. In the case of both natural and synthetic HPX, the fragments and analogs will preferably retain at least a portion of the native biological activity, i.e. the ability to stimulate the growth or repair of hepatocytes in vitro and in vivo.

Synthetic polypeptides representing intact hemopoietin X or a biologically active fragment or analog thereof may be prepared synthetically by either of two general approaches. First, polypeptides having a length up to the entire length of HPX may be synthesized by the well-known Merrifield solid-phase method where amino acids are sequentially added to a growing chain, Merrifield (1963) J. Am. Chem. Soc. 85:2149–2156. Commercial systems for the automated synthesis of such polypeptides are available.

The second and generally preferred method for synthesizing HPX polypeptides according to the present invention involves expression in cultured cells of recombinant DNA molecules encoding all or a portion of the HPX protein. The recombinant DNA molecule may incorporate either a natural or synthetic gene, with natural genes and cDNA being obtainable from hepatocytes, preferably fetal hepatocytes, as described above. Alternatively, polynucleotides may be synthesized by well-known techniques as described in the technical literature. See, e.g. Carruthers et al., Cold Spring Harbor Symp. Quant. Biol. 47:411–418, 1982, and Adams et al., J. Am. Chem. Soc. 105:661, 1983, both of which are incorporated herein by reference. Double-stranded fragments may then be obtained either by synthesizing the complementary strand and annealing the strands together under appropriate conditions, or by adding the complementary strand using DNA polymerase with an appropriate primer sequence.

The natural or synthetic DNA fragments encoding the desired HPX fragment or analog thereof will be incorporated in a DNA construct capable of introduction to and expression in in vitro cell culture. Usually, the DNA constructs will be suitable for replication in a unicellular host, such as yeast or bacteria. Alternatively, the DNA constructs may be suitable for introduction and integration within the genome of mammalian cells, preferably human cells, typically by cotransfection with a marker selectable in the cells. DNA constructs prepared for the introduction into bacteria or yeast will include a replication system recognized by the host, the DNA coding the desired polypeptide, transcriptional and translational initiation and regulatory sequences joined to the 5'-end of the DNA fragment, and transcriptional and translational termination regulatory sequences joined to the 3'-end fragment. Such recombinant expression systems are widely described in the literature and commercially available from numerous suppliers.

The isolated and purified HPX polypeptides of the present invention may be utilized in vitro for the stimulation of hepatocyte growth and cell culture. Typically, the HPX polypeptides will be added to cell culture to concentration in the range from about 0.01 pg/ml to 1 μg/ml, usually from about 1 ng/ml to 10 ng/ml, resulting in stimulation of hepatocyte proliferation. Such in vitro stimulation of hepatocyte growth will be useful in a variety of circumstances, including the growth of genetically altered hepatocytes for use in gene therapy applications.

The isolated and purified HPX polypeptides of the present invention may also be incorporated as components in pharmaceutical compositions useful to treat various liver diseases and conditions, such as acute and chronic hepatitis, alcoholic liver disease, hepatic dysfunction resulting from sepsis, liver toxemia, and the like. Such pharmaceutical compositions should contain a therapeutic amount of at least one HPX polypeptide according to the present invention present in a pharmaceutically acceptable carrier. By a "therapeutic amount" it is meant that sufficient HPX polypeptide will be present in order to treat the disease or condition by stimulating in vivo growth or repair hepatocytes when administered to a host. Typically, the HPX will be present in the carrier at concentrations in the range from about 0.1 µg/ml to 100 µg/ml, usually in the range from about 1 µg/ml to 10 µg/ml.

The pharmaceutically acceptable carrier can be any compatible, non-toxic substance suitable to deliver the HPX polypeptide to the patient. Sterile water, alcohol, fats, waxes, and inert solids may be used as the carrier. Pharmaceutically acceptable adjuvants, buffering agents, dispersing agents, and the like, may also be incorporated into the pharmaceutical compositions. Such compositions can contain a single HPX polypeptide or two or more HPX polypeptides according to the present invention. The pharmaceutical compositions just described are useful for oral or parenteral administration. Preferably, the compositions will be administered parenterally, i.e. subcutaneously, intravascularly, or intravenously. Alternate modes of administration may also be employed, such as nasal delivery, respiratory delivery, transdermal delivery, and the like. Usually, the total dosage of HPX will be based on the host's body weight, typically being in the range from about 0.001 mg/kg to 1 mg/kg, usually being in the range from about 0.01 mg/kg to 0.1 mg/kg.

The following examples are offered by way of illustration, not by way of limitation.

EXPERIMENTAL

1. Purification of HPX

Fetal liver was derived from an aborted fetus of 4–5 months gestation. A single cell suspension was prepared in saline. The sedimented cells collected after centrifugation at 800 g for 15 min. were lysed by addition of 250 ml of distilled water (35% w/v) and kept at −20° C. overnight. After thawing, lysate was heated to 95° C. for 15 min. followed by centrifugation for 30 min. at 4000 g. The transparent crude supernatant was designated and fetal liver lysate (FLL) was used for further isolation and purification of the hepatopoietin.

Figure 2:
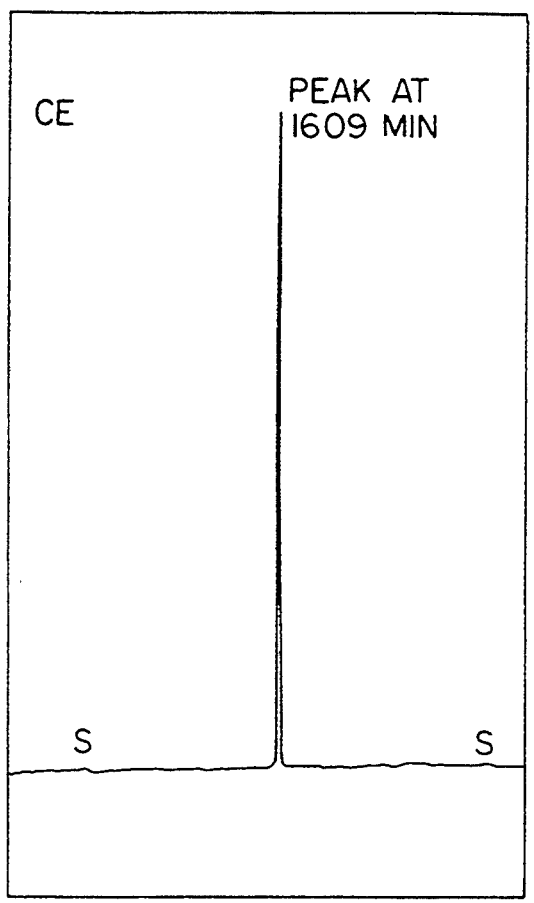
FIG. 2 is a capillary electrophoresis profile of HK-4, as described in the Experimental section hereinafter.

FLL was purified by the scheme set forth in Table 1. The FLL was first ultrafiltered through membrane filters with molecular sizes of 10 kD, 30 kD and 60 kD. Most of the HK activity was in the 10–30 kD range (denoted HK-1). In some cases, a Bio-Gel-P10 column was used in place of the filtration step. Further purification procedures included DEAE-cellulose chromatography (denoted HK-2), FPLC using a mono Q column (denoted HK-3) followed by an HPLC TSK GEL2000SW column (denoted HK-4). All preparations were dialyzed against water and lyophilized prior to assay. A Coomassie stained SDS-PAGE showed a single band at approximately 15 kD for the final HK-4 material (FIG. 1; Lane A). A single symmetrical peak was found on capillary electrophoresis (FIG. 2).

TABLE 1

| Purification of FLL | | | |
|---|---|---|---|
| Purification Step | Active Fraction Designation | Protein Recovery (mg) | Bioactivity[1] (U/mg) |
| Filtrate after ultra-filtration (MW<60 kD) | | 8000 | 1 |
| Bio-Gel ® P10 | HK-1 | 500 | 380 |
| DEAE-cellulose | HK-2 | 6.0 | 1186 |
| Mono-Q (FPLC) | HK-3 | 0.2 | 6953 |

TABLE 1-continued

| Purification of FLL | | | |
|---|---|---|---|
| Purification Step | Active Fraction Designation | Protein Recovery (mg) | Bioactivity[1] (U/mg) |
| TSK G2000SW (HPLC) | HK-4 | 0.1 | 20,000 |

[1]Measured by assay described in Section 2, below.

2. Bioassay of Hepatokine Activity

Human hepatoma cell line SMMC-7721 (Dong et al. (1980) Bulletin 2nd. Military Med. Univ. 1:5–10) and adult hepatocyte cell line HL-7702 (Ye et al. (1980) Acta Exp. Biol. 13:361–367) were maintained in RPMI-1640 containing 15% newborn calf serum. Hepatokine bioactivity was determined using $^3$H-TdR incorporation by the SMMC-7721 hepatoma line. One unit (U) of stimulating activity was defined as a 50% cpm count increase over unstimulated control values. Both the highly purified hepatopoietin (HK-4) and the oocyte-derived hepatopoietin (see section 4 below) were mitogenic for SMMC-7721 and HL-7702 hepatocyte cell lines, human and mouse fetal liver cells (Table 2), but not for human K562 cells, NH3T3 cells, or human fetal kidney or human fetal spleen cells (data not shown). Insulin, glucagon, and epidermal growth factor were not mitogenic for the SMMC-7721 cells (data not shown).

TABLE 2

| In vitro Activity of Highly Purified HPX (HK-4) | | | |
|---|---|---|---|
| Cells | Control (0 ng/ml) | 20 ng/ml | 40 ng/ml |
| SMMC-7721 | 2076 ± 105† | 4202 + 239* | 7394 + 522* |
| Human fetal liver | 326 ± 78 | 751 ± 161* | 997 ± 174* |
| Human fetal spleen | 482 ± 123 | 425 ± 237 | — |
| Human fetal kidney | 417 ± 208 | 396 ± 168 | |

N = 6
*p < 0.001 versus control
†cpm $^3$H-thymidine incorporation ±SD

3. Biochemical Characteristics of HPX

HPX is resistant to heating (95° C., 30 min), acid (pH 2), alkali (pH9) and enzymes including neuraminidase, RNase, DNase (Table 3). HPX is sensitive to proteinase K. The protein pI has a pI of approximately 6.0 on isoelectric focusing (data not shown).

TABLE 3

| Physicochemical Properties of Hepatopoietin (fraction HK-4) | |
|---|---|
| Treatment | Activity† |
| RPMI-1640 (negative control) | 1807 ± 134* |
| RPMI-1640 (positive control) | 4472 ± 477 |
| 95° C., 15 min | 4913 ± 546 |
| proteinase K, 37° C., 30 min | 1252 ± 318* |
| neuraminidase, 37°C., 30 min | 4900 ± 543 |
| DNase, 37° C., 30 min | 4558 ± 371 |
| RNase, 37° C., 30 min | 4616 ± 326 |
| 0.1% SDS | 4348 ± 413 | n = 6
*p < 0.01
†cpm/2 × $10^5$ SMMC-7721 cells

4. Activity of Human Fetal Liver mRNA in Xenopus laevis Oocytes.

Figure 3:
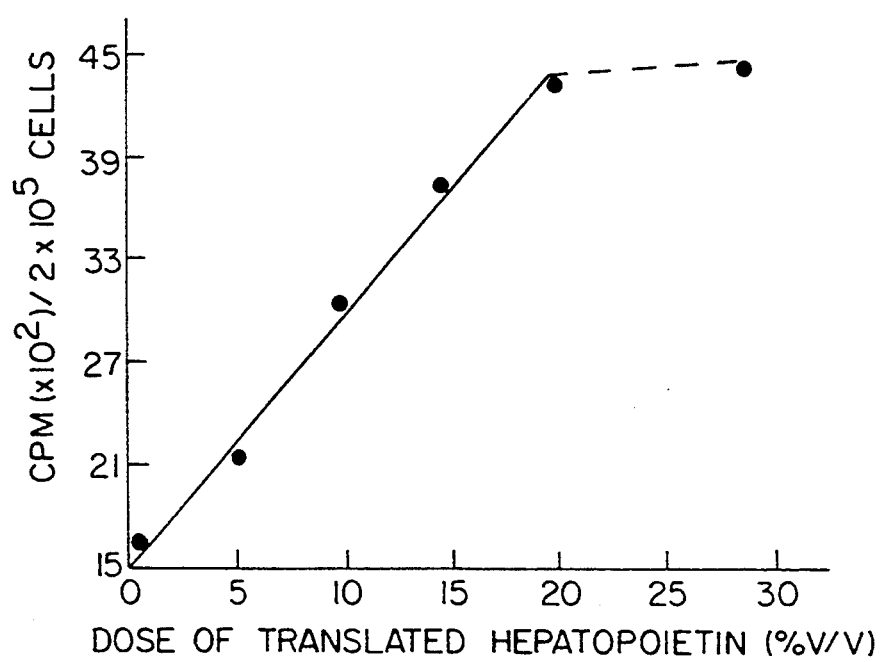
FIG. 3 is a graph illustrating the dose response of oocyte-derived HPX on the mitogenic stimulation of SMMC-7721 hepatocytes.

Total RNA was prepared from poly (A)+mRNA liver tissue from a human fetus of 4–5 months gestation using standard techniques. Poly (A)+mRNA was prepared using an oligo(dT)-cellulose column. Single Xenopus laevis oocytes were microinjected with 50 nl of poly (A)+mRNA (1 ng/nl). Supernatant and lysate (prepared by freeze/thaw and cleared by 13,000 g sedimentation) from groups of 20 oocytes were ultrafiltered by millipore filters (10–30 kD range). Supernatant and lysate from saline injected (i.e. control) oocytes did not stimulate or inhibit growth of SMMC-7721 cells. This may be due to the presence of cell growth inhibitors such as arginase (>30kD) or low molecular weight inhibitors (<10kD) in the crude preparation. Total lysate of poly(A)+mRNA injected oocytes demonstrated no effect on the SMMC-7721 cells. However, following fractionation by ultrafiltration, hepatopoietin activity was found in the 10–30 kD fraction. FIG. 3 demonstrates a linear mitogenic effect of fractionated oocyte lysate on SMMC-7721 cells. No mitogenesis was observed on HL60, K562 or NIH3T3 cells (data not shown) suggesting that the factor was hepatocyte specific, unlike interleukin 6 (IL6), fibroblast growth factor (FGF) or insulin-like growth factor (IGF) where the mitogenic activity is not specific to hepatocytes (He et al. (1990) Chinese J. Appl. Physiol. 6:298–302; and Wei et al. (1989) Exp. Hematol. 17:1044–1046).

5. Amino Acid and N-terminal Amino Acid Sequence Analysis.

HPX purified to homogeneity was subjected to hydrolysis and amino acid analysis (Table 5) and automated Edman degradation to determine the N-terminal amino acid sequence. No sequence was forthcoming, indicating that the N-terminus is blocked.

TABLE 5

| Amino Acid Composition of HPX | | | | | |
|---|---|---|---|---|---|
| Amino Acid | nMol | Amino Acid | nMol | Amino Acid | nMol |
| ALA | 1.404 | ASP | 2.478 | ARG | 0.407 |
| GLU | 2.826 | GLY | 2.899 | PRO | 1.646 |
| TYR | 0.889 | SER | 1.638 | HIS | 10.284 |
| THR | 1.295 | MET | 3.856 | CYS | present |
| ILE | 8.161 | LYS | 0.749 | PHE | 0.854 |

TABLE 5-continued

| Amino Acid Composition of HPX | | | | | |
|---|---|---|---|---|---|
| Amino Acid | nMol | Amino Acid | nMol | Amino Acid | nMol |
| VAL | 1.351 | | | | |

6. HPX Protects Mice from Acute Liver Injury.

Figure 4:
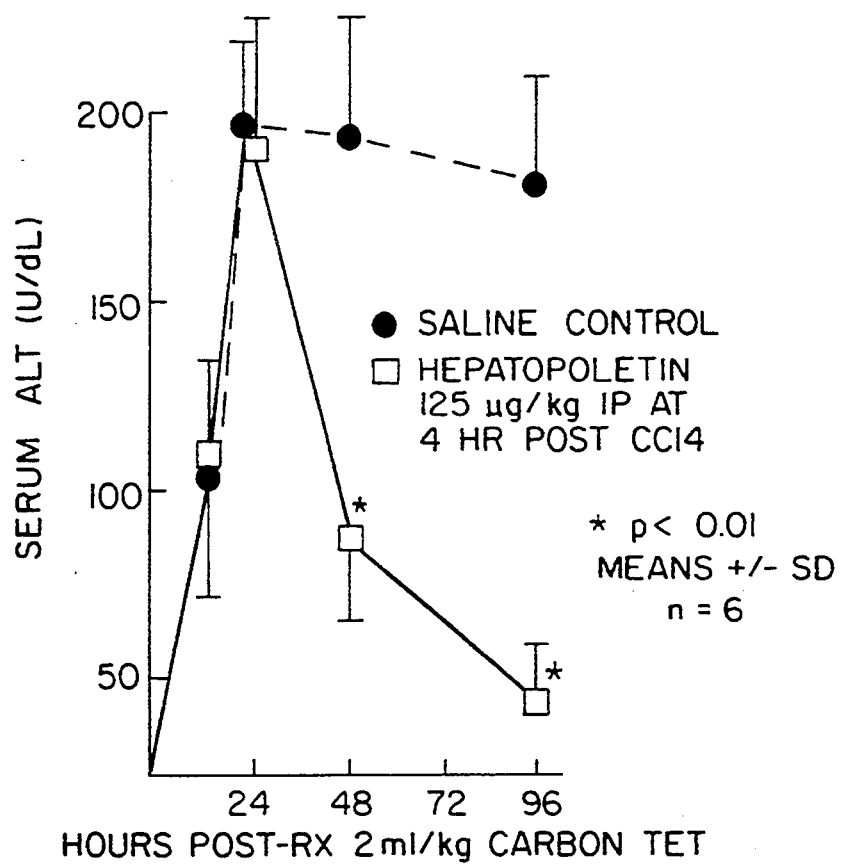
FIG. 4 is a graph of serum glutamic-pyruvic transaminase (ALT) levels in mice injected with carbon tetrachloride and treated with saline (●) or HPX (□).
Figure 5:
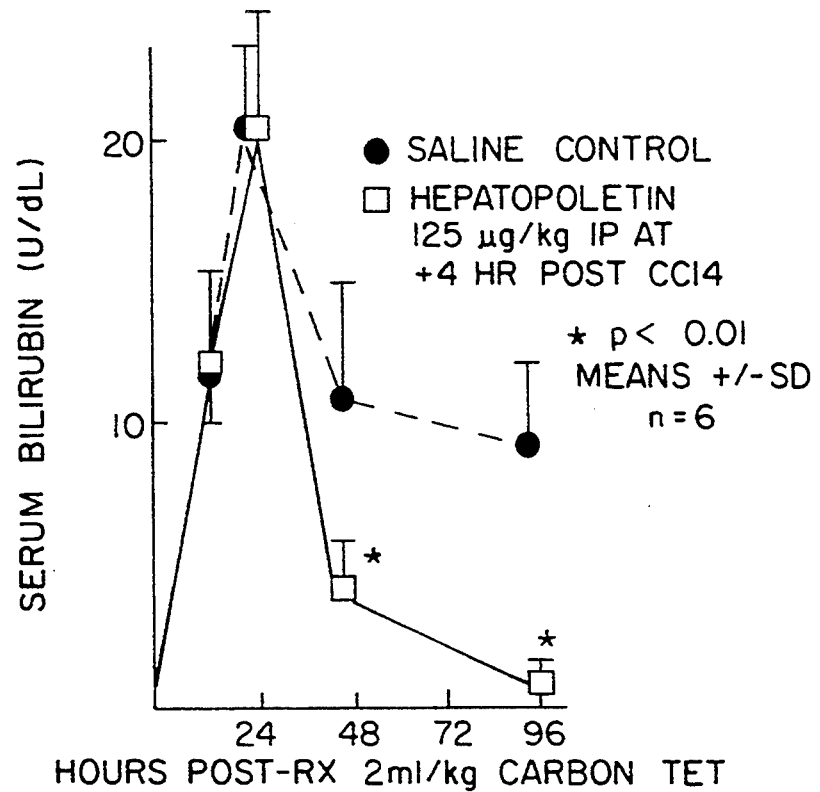
FIG. 5 is a graph of serum bilirubin levels in mice injected with carbon tetrachloride and treated with saline (●) or HPX (□).

C57BL/6 mice, 10–14 weeks old, were injected IP with 50% $CCl_4$ (4ml/kg). Four hours later, mice were randomly given various preparations of HPX (Table 6). Animal mortality was recorded at 72 hr. Serum bilirubin (BIL) and glutamic-pyruvic transaminase (ALT) levels, $^3$H-TdR incorporation rate in vivo, and histological examination of liver tissue revealed a protective effect of HPX (see FIGS. 4 and 5 for ALT and BIL results, respectively). As shown in Table 6, highly purified HPX protected mice from lethal carbon tetrachloride-induced hepatic failure and death.

TABLE 6

| HPX Protects Mice from $CCl_4$ Toxicity | | | | | |
|---|---|---|---|---|---|
| Substance Injected | Delivery Route | Injected Protein (mg/kg) | Hepatopoietin Activity (U) | Mice (number) | Mortality (%) |
| Saline | IP | 0 | 0 | 20 | 60 |
| Saline | IV | 0 | 0 | 10 | 70 |
| HK-1 | IP | 50 | 2500 | 18 | 11* |
| HK-2 | IP | 0.125 | 2500 | 9 | 0* |
| HK-3 | IV | 0.125 | 2500 | 6 | 0* |

*$p < 0.05$

Although the foregoing invention has been described in detail for purposes of clarity of understanding, it will be obvious that certain modifications may be practiced within the scope of the appended claims.

What is claimed is:

1. An isolated and purified human protein having hepatocyte stimulating activity and characterized by the gel pattern of FIG. 1 and the amino acid composition of Table 5.

2. Human protein as in claim 1, purified to at least 10% w/w.

* * * * *